(12) United States Patent
Toriumi

(10) Patent No.: US 11,820,755 B2
(45) Date of Patent: Nov. 21, 2023

(54) URACIL COMPOUND AND USE THEREOF

(71) Applicant: Sumitomo Chemical Company, Limited, Tokyo (JP)

(72) Inventor: Tatsuya Toriumi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 284 days.

(21) Appl. No.: 17/257,187

(22) PCT Filed: Jul. 4, 2019

(86) PCT No.: PCT/JP2019/026690
§ 371 (c)(1),
(2) Date: Dec. 30, 2020

(87) PCT Pub. No.: WO2020/009193
PCT Pub. Date: Jan. 9, 2020

(65) Prior Publication Data
US 2021/0122731 A1   Apr. 29, 2021

(30) Foreign Application Priority Data

Jul. 5, 2018 (JP) .................................. 2018-128121

(51) Int. Cl.
*C07D 401/12* (2006.01)
*A01N 43/54* (2006.01)

(52) U.S. Cl.
CPC ........... *C07D 401/12* (2013.01); *A01N 43/54* (2013.01)

(58) Field of Classification Search
None
See application file for complete search history.

(56) References Cited

U.S. PATENT DOCUMENTS

| | | | |
|---|---|---|---|
| 5,280,010 A | 1/1994 | Enomoto et al. | |
| 7,157,579 B2 * | 1/2007 | Tohyama | C07D 401/12 544/310 |
| 7,993,678 B2 | 8/2011 | Tommeraas et al. | |
| 2004/0254077 A1 | 12/2004 | Tohyama et al. | |

FOREIGN PATENT DOCUMENTS

| | | |
|---|---|---|
| JP | H04360876 A | 12/1992 |
| JP | H05155866 A | 6/1993 |
| JP | 2009510186 A5 | 3/2009 |
| JP | 5155866 B2 | 3/2013 |
| MY | 105303 A | 9/1994 |
| WO | 9109859 A1 | 7/1991 |
| WO | 2003014109 A1 | 2/2003 |

OTHER PUBLICATIONS

English Translation of International Preliminary Report on Patentability dated Jan. 5, 2021 in International Application No. PCT/JP2019/026690.
English Translation of International Search Report dated Oct. 1, 2019 in International Application No. PCT/JP2019/026690.
Turner, J. A., A World Compendium; The Pesticide Manual—Seventeenth Edition, Index 4, British Crop Production Council, 9 pages (2015).
Examination Report dated Jul. 6, 2022 in IN Application No. 202147000043.

* cited by examiner

*Primary Examiner* — Erin E Hirt

(74) *Attorney, Agent, or Firm* — Panitch Schwarze Belisario & Nadel LLP

(57) ABSTRACT

A compound represented by formula (A) has excellent control efficacy against plant diseases.

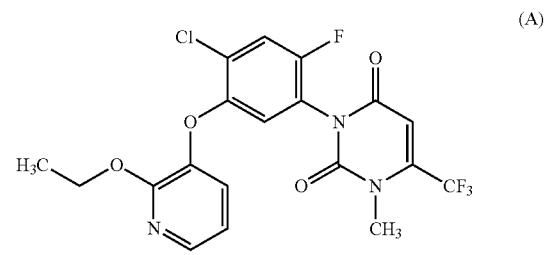

(A)

2 Claims, No Drawings

URACIL COMPOUND AND USE THEREOF

CROSS-REFERENCE TO RELATED APPLICATIONS

This application is a Section 371 of International Application No. PCT/JP2019/026690, filed Jul. 4, 2019, which was published in the Japanese language on Jan. 9, 2020 under International Publication No. WO 2020/009193 A1, which claims priority under 35 U.S.C. § 119(b) to Japanese Application No. 2018-128121, filed on Jul. 5, 2018, the disclosures of which are incorporated herein by reference in their entireties.

TECHNICAL FIELD

The present invention relates to a uracil compound and use thereof.

BACKGROUND ART

Conventionally, in order to control plant diseases, various compounds have been developed and come into practical use (see Non-patent document 1). Also, a compound represented by formula (B):

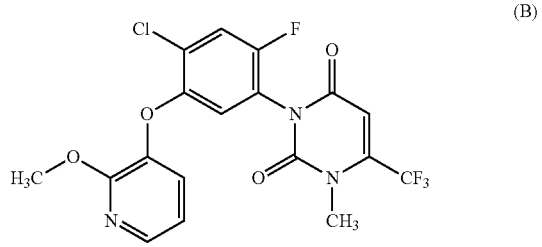 [SMILES: COc1ncccc1Oc1cc(-n2c(=O)cc(C(F)(F)F)n(C)c2=O)c(F)cc1Cl]

(hereinafter referred to as Compound B) is described as an intermediate for preparing an herbicide (see Patent document 1).

CITATION LIST

Patent Document

Patent Document 1: U.S. Pat. No. 7,157,579 B2

Non-Patent Document

Non-Patent Document 1: The Pesticide Manual—17th edition (published by BCPC) ISBN 978-1-901396-88-1

SUMMARY OF THE INVENTION

Problems to be Solved by Invention

An object of the present invention is to provide a compound having excellent control effect on plant diseases.

Means to Solve Problems

The present inventor has intensively studied the above-mentioned problems, and found that a compound represented by the following formula (A) has some excellent efficacy on controlling plant diseases, which thus completed the present invention.

The present invention is as follows.

[1] A compound represented by formula (A):

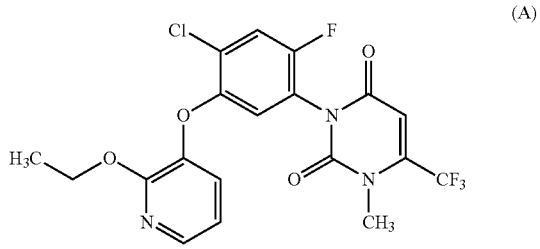

(hereinafter referred to as "Compound A").

[2] A composition comprising the compound according to the above [1] and an inert carrier (hereinafter, referred to as "Present composition" or "Composition of the present invention").

[3] A method for controlling a plant disease which comprises applying an effective amount of the compound according to the above [1] to a plant or a soil for cultivating the plant (hereinafter, referred to as "Present control method" or "Control method of the present invention").

Effect of Invention

The present invention can control plant diseases.

MODE FOR CARRYING OUT THE INVENTION

The composition of the present invention comprises the compound A and an inert carrier. The composition of the invention is usually prepared by mixing the compound A with the inert carrier such as a solid carrier and a liquid carrier and the like, and if necessary, adding a surfactant and other auxiliary agents for formulation to formulate into emulsifiable concentrates, oil solutions, powders, granules, wettable powders, water dispersible granules, flowables, dry flowables, microcapsules and the others.

The composition of the present invention usually comprises 0.0001 to 95% by weight of the compound A.

Examples of the solid carrier to be used in the formulation include fine powders or granules of clays (for example, kaolin clay, diatomaceous earth, bentonite, or acid white clay), dry silica, wet silica, talcs, ceramics, other inorganic minerals (for example, sericite, quartz, sulfur, active carbon, or calcium carbonate), or chemical fertilizers (for example, ammonium sulfate, ammonium phosphate, ammonium nitrate, urea, or ammonium chloride) and the others, as well as synthetic resins (for example, polyester resins such as polypropylene, polyacrylonitrile, polymethyl methacrylate or polyethylene terephthalate; nylon resins (for example, nylon-6, nylon-11 or nylon-66); polyamide resins; polyvinyl chloride, polyvinylidene chloride, vinyl chloride-propylene copolymers, and the others).

Examples of the liquid carriers include water; alcohols (for example, methanol or ethanol); ketones (for example, acetone or methyl ethyl ketone); aromatic hydrocarbons (for example, toluene or xylene); aliphatic hydrocarbons (for example, hexane or cyclohexane); esters (for example, ethyl acetate or butyl acetate); nitriles (for example, acetonitrile); ethers (for example, diisopropyl ether or diethyleneglycol dimethylether); amides (for example, N,N-dimethylformamide); sulfoxides (for example, dimethyl sulfoxide); and vegetable oils (for example, soybean oil or cottonseed oil).

Examples of the surfactants include nonionic surfactants such as polyoxyethylenated alkyl ethers, polyoxyethylenated alkyl aryl ether, and polyethylene glycol fatty acid ester; and anionic surfactants such as alkyl sulfonates, alkylbenzene sulfonates and alkyl sulfates.

Examples of the other auxiliary agents for formulation include, a binder, a dispersant, a colorant, and a stabilizer, and specific examples thereof include casein, gelatin, polysaccharides (for example, starch, gum arabic, cellulose derivatives, or alginic acid), lignin derivatives, bentonite, water-soluble synthetic polymers (for example, polyvinyl alcohol, polyvinyl pyrrolidone, polyacrylic acids or); acidic isopropyl phosphate, 2,6-di-tert-butyl-4-methylphenol, and BHA (a mixture of 2-tert-butyl-4-methoxyphenol and 3-tert-butyl-4-methoxyphenol).

The compound A has efficacies against plant pathogens. The plant diseases derived from plant pathogens include the followings. The descriptions in the below-mentioned parenthesis represent a scientific names of the pathogenic fungi which causes the corresponding diseases.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: leaf stripe (*Septoria tritici*), powdery mildew (*Blumeriagraminis*), Fusarium head blight (*Fusarium graminearum, Fusarium avenaceum, Fusarium culmorum, Microdochium nivale*), yellow rust (*Puccinia striiformis*), black rust (*Puccinia graminis*), blown rust (*Puccinia recondita*), snow mold (*Microdochium nivale, Microdochium majus*), Typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), glume blotch (*Stagonospora nodorum*), tan spot (*Pyrenophora tritici-repentis*), damping-off caused by *Rhizoctonia* fungus (*Rhizoctonia solani*), and take-all disease (*Gaeumannomyces graminis*);

Barley diseases: powdery mildew (*Blumeria graminis*), Fusarium head blight (*Fusarium graminearum, Fusarium avenaceum, Fusarium culmorum, Microdochium nivale*), yellow rust (*Puccinia striiformis*), black rust (*Puccinia graminis*), blown rust (*Puccinia hordei*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off caused by *Rhizoctonia* fungus (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eye spot (*Kabatiella zeae*), Phaeosphaeria leaf spot disease (*Phaeosphaeria maydis*), Diplodia (*Stenocarpella maydis, Stenocarpella macrospora*), stalk rot (*Fusarium graminearum, Fusarium verticilioides, Colletotrichum graminicola*), and smut (*Ustilago maydis*);

Cotton diseases: anthracnose (*Colletotrichum gossypii*), grey mildew (*Ramularia areola*), *Alternaria* leaf spot (*Alternaria macrospora, Alternaria gossypii*), and black root rot caused by *Thielaviopsis* fungus (*Thielaviopsis basicola*);

Coffee diseases: rust (*Hemileia vastatrix*), and leaf spot (*Cercospora coffeicola*);

Rapeseed diseases: Sclerotinia rot (*Sclerotinia sclerotiorum*), gay leaf spot (*Alternaria brassicae*), and *Phoma* stem canker and *Phoma* leaf spot (*Phoma lingam*);

Sugarcane disease: rust (*Puccinia melanocephela, Puccinia kuehnii*);

Sunflower diseases: rust (*Puccinia helianthi*), and downy mildew (*Plasmopara halstedii*);

Citrus diseases: melanose (*Diaporthe citri*), scab (*Elsinoe fawcetti*), green mold (*Penicillium digitatum, Penicillium italicum*), and *Phytophthora* disease (*Phytophthora parasitica, Phytophthora citrophthora*);

Apple diseases: blossom blight (*Monilinia mali*), Valsa canker (*Valsa ceratosperma*), powdery mildew (*Podosphaera leucotricha*), *Alternaria* leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophtora cactorum*);

Pear diseases: scab (*Venturia nashicola, Venturia pirina*), black spot (*Alternaria alternata* Japanese pear pathotype), and rust (*Gymnosporangium haraeanum*);

Peach diseases: brown rot (*Monilihia fructicola*), scab (*Cladosporium carpophilum*), and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*), and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), Fusarium wilt (*Fusarium oxysporum*), downy mildew (*Pseudoperonospora cubensis*), *Phytophthora* rot (*Phytophthora* sp.), and damping-off (*Pythium* sp.);

Tomato diseases: early blight (*Alternaria solani*), leaf mold (*Cladosporium fulvum*), *Cercospora* leaf mold (*Pseudocercospora fuligena*), late blight (*Phytophthora infestans*), and powdery mildew (*Leveillula taurica*);

Eggplant diseases: brown spot (*Phomopsis vexans*), and powdery mildew (*Erysiphe cichoracearum*);

Diseases of brassica family: *Alternaria* leaf spot (*Alternaria japonica*), white spot (*Cercosporella brassicae*), clubroot (*Plasmodiophora brassicae*), and downy mildew (*Peronospora parasitica*);

Welsh onion disease: rust (*Puccinia allii*);

Soybean diseases: *Cercospora* leaf blight and purple stain (*Cercospora kikuchii*), Sphaceloma scab (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, Colletotrichum truncatum*), Rhizoctonia rot (*Rhizoctonia solani*), Septoria brown spot (*Septoria glycines*), frog eye leaf spot (*Cercospora sojina*), stem rot (*Sclerotinia sclerotiorum*), powdery mildew (*Microsphaera diffusa*), *Phytophthora* root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown Leaf spot (*Cercospora arachidicola*), and southern blight (*Sclerotium rolfsii*);

Garden pea disease: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranean* f. sp. *subterranea*), and *Verticillium* wilt (*Verticillium alboatrum, Verticillium dahliae, Verticillium nigrescens*);

Strawberry disease: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theae-sinensis*);

Tobacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: *Cercospora* leaf spot (*Cercospora beticola*), leaf blight (*Thanatephorus cucumeris*), root rot (*Thanatephorus cucumeris*), *Aphanomyces* root rot (*Aphanomyces cochlioides*), and rust (*Uromyces betae*);

Rose diseases: black spot (*Diplocarpon rosae*), and powdery mildew (*Sphaerotheca pannosa*);

Chrysanthemum diseases: leaf blight (*Septoria chrysanthemi-indici*), and white rust (*Puccinia horiana*);

Onion diseases: *Botrytis* leaf blight (*Botrytis cinerea, Botrytis byssoidea, Botrytis squamosa*), gray-mold neck rot (*Botrytis allii*), and small sclerotial (*Botrytis squamosa*);

Various crops diseases: *Sclerotinia* rot (*Sclerotinia sclerotiorum*);

Japanese radish disease: *Alternaria* leaf spot (*Alternaria brassicicola*);

Turfgrass diseases: dollar spot (*Sclerotinia homoeocarpa*), and brown patch and large patch (*Rhizoctonia solani*);

Banana disease: Sigatoka disease (*Mycosphaerella fijiensis, Mycosphaerella musicola*);

Seed diseases or diseases in the early stage of the growth of various crops caused by the fungi of genera of *Aspergillus, Penicillium, Fusarium, Gibberella, Tricoderma, Thielaviopsis, Rhizopus, Mucor, Corticium, Phoma, Rhizoctonia, Diplodia*, and the others;

Viral diseases of various crops mediated by genera of *Polymixa, Olpidium*, and the others;

Rice damping-off (*Burkholderia plantarii*);

Cucumber cucumber bacterial spot (*Pseudomonas syringae* pv. *Lachrymans*);

Eggplant bacterial wilt (*Ralstonia solanacearum*);

Citrus canker (*Xanthomonas citiri*);

Chinese cabbage slimy soft rot (*Erwinia carotovora*);

and the others.

The method for controlling plant diseases of the present invention includes, for example, an application to plants such as a foliage application and seed disinfection and the others; and an application to area for cultivating plants such as a submerged treatment.

An application dose of the compound A is usually within a range of 1 to 10,000 g per 1,000 m². When the compound A is formulated into emulsifiable concentrates, wettable powders, and flowables, and the others, such formulations are usually applied after diluting it with water in such a way that the concentration of the active ingredient is within a range from 0.01 to 10,000 ppm and, in the case of being formulated into dust formulations, granules, and the others, such formulations are usually used at itself.

The composition of the invention may be used as an agent for controlling plant diseases in agricultural lands such as fields, paddy fields, turfs, and orchards.

EXAMPLES

Hereinafter, the present invention is explained in more detail by using Preparation Example, and Test Example and the like, however, the present invention should not be limited to these examples. The Preparation Examples of the compound A is shown below.

Reference Preparation Example

A mixture of 10.0 g of 3-{2-Chloro-4-fluoro-5-[3-methyl-2,6-dioxo-4-(trifluoromethyl)-1,2,3,6-tetrahydropyrimidin-1-yl]phenoxy}-2-hydroxypyridine, which was prepared by the method described in the Description of the U.S. Pat. No. 7,157,579 B2, and 17.8 g of phosphorus oxychloride was stirred at 80° C. for 3 hours. Water was added to the resulting mixture and then the mixture was extracted with ethyl acetate. The resulting organic layer was concentrated under reduced pressure. The resulting residue was subjected to a silica gel chromatography to obtain the intermediate A represented by the following formula 7.35 g.

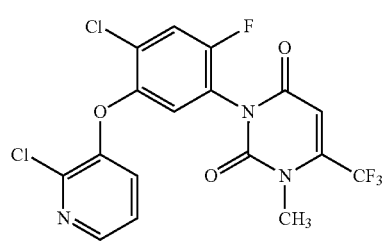

Intermediate A

Preparation Example

A mixture of 2.00 g of the intermediate A, 0.05 g of palladium (II) acetate, 0.19 g of 2-di-tert-butylphosphino-2',4',6'-triisopropylbiphenyl, 0.75 g of potassium tert-butoxide, 8.01 g of toluene and 4.00 g of ethanol was stirred at 70° C. for 4 hours under nitrogen atmosphere. The resulting mixture was concentrated under reduced pressure. Ethyl acetate was added to the resulting residue, and the mixture was washed successively with saturated aqueous sodium bicarbonate and water. The resulting organic layer was concentrated under reduced pressure. The resulting residue was subjected to a silica gel chromatography to obtain 0.53 g of the compound A.

The $^1$H-NMR data of the compound A is shown below.

$^1$H-NMR (CDCl$_3$) δ (ppm): 7.96 (1H, dd, J=4.9, 1.6 Hz), 7.38 (1H, d, J=8.8 Hz), 7.27-7.24 (1H, m), 6.85 (1H, dd, J=7.9, 4.9 Hz), 6.68 (1H, d, J=6.6 Hz), 6.31 (1H, s), 4.39 (2H, q, J=7.0 Hz), 3.52 (3H, s), 1.31 (3H, t, J=7.0 Hz).

Next, Test examples are shown below.

Test Example 1

Each 1 μL of a solution containing the compound A at a predetermined concentration in dimethylsulfoxide was dispensed into a titer plate (96 wells), and then each 150 μL of potato broth medium containing suspension of spore of wheat leaf stripe fungi (*Septoria tritici*) was dispensed so that the concentration of the compound A was finally 4.7 ppm. The plate was cultured at 18° C. for 4 days, thereby allowing the wheat leaf stripe fungi to undergo proliferation, and the absorbance at 600 nm of each well of the titer plate was then measured to determine a degree of growth of the wheat leaf stripe fungi. The efficacy was calculated from the determined degree of growth by the below-mentioned "Equation 1".

$$\text{Efficacy (\%)} = 100 \times (X-Y)/X \quad \text{"Equation 1"}$$

wherein

X: Degree of fungal growth in non-treated area
Y: Degree of fungal growth in treated area The "Non-treated area" represents an area where a similar treatment procedure to that of the treated area except for not using the compound A is done.

As a result, the efficacy was 73%.

Test Example 2

Each 1 μL of a solution containing the compound A at a predetermined concentration in dimethylsulfoxide was dispensed into a titer plate (96 wells), and then each 150 μL of potato broth medium containing suspension of spore of wheat leaf stripe fungi was dispensed so that the concentration of the compound A was finally 1.2 ppm. The plate was cultured at 18° C. for 4 days, thereby allowing the wheat leaf stripe fungi to undergo proliferation, and the absorbance at 600 nm of each well of the titer plate was then measured to determine a degree of growth of the wheat leaf stripe fungi. The efficacy was calculated from the determined degree of growth by the below-mentioned "Equation 1". As a result, the efficacy was 53%.

Test Example 3

Each 1 μL of a solution containing the compound A at a predetermined concentration in dimethylsulfoxide was dispensed into a titer plate (96 wells), and then each 150 μL of potato broth medium containing suspension of spore of barley scald fungi (*Rhynchosporium secalis*) was dispensed so that the concentration of the compound A was finally 4.7 ppm. The plate was cultured at 18° C. for 7 days, thereby allowing the barley scald fungi to undergo proliferation, and the absorbance at 600 nm of each well of the titer plate was then measured to determine a degree of growth of the barley scald fungi. The efficacy was calculated from the determined degree of growth by the below-mentioned "Equation 1". As a result, the efficacy was 94%.

Comparative Test Example 1

The test was carried out according to Test Example 1 using the compound B instead of the compound A. As a result, the efficacy was 45%.

Comparative Test Example 2

The test was carried out according to Test Example 2 using the compound B instead of the compound A. As a result, the efficacy was 12%.

Comparative Test Example 3

The test was carried out according to Test Example 3 using the compound B instead of the compound A. As a result, the efficacy was 41%.

INDUSTRIAL APPLICABILITY

The compound A shows an excellent control effect against plant diseases.

The invention claimed is:

1. A compound represented by formula (A):

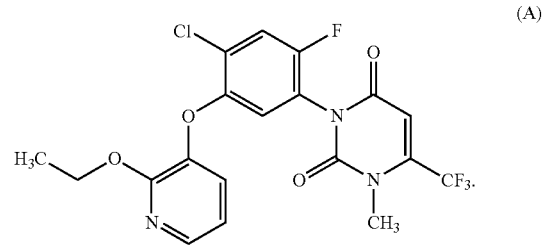 [SMILES: CCOc1ncccc1Oc1cc(-n2c(=O)cc(C(F)(F)F)n(C)c2=O)c(F)cc1Cl]

(A)

2. A composition comprising a compound represented by formula (A):

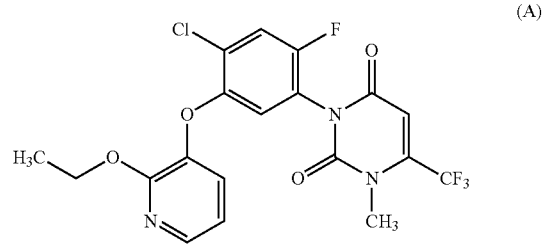 [SMILES: CCOc1ncccc1Oc1cc(-n2c(=O)cc(C(F)(F)F)n(C)c2=O)c(F)cc1Cl]

(A)

and an inert carrier.

* * * * *